United States Patent
Chang et al.

(10) Patent No.: US 9,552,517 B2
(45) Date of Patent: Jan. 24, 2017

(54) TRACKING EYE RECOVERY (71) Applicant: INTERNATIONAL BUSINESS MACHINES CORPORATION, Armonk, NY (US)

(72) Inventors: Hung-Yang Chang, Scarsdale, NY (US); Pei-yun S Hsueh, New York, NY (US); Lih-Guong Jang, Hsinchu (TW); Joe Lu, Taipei (TW); Sreeram Ramakrishnan, Lynnfield, MA (US); Yi-Chang Wang, Tainan (TW); Nien-Chu Wu, Taoyuan County/Longtan Township (TW); Xinxin Zhu, Croton-on-Hudson, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 165 days.

(21) Appl. No.: 14/099,326

(22) Filed: Dec. 6, 2013

(65) Prior Publication Data

US 2015/0161783 A1 Jun. 11, 2015

(51) Int. Cl.
*G06K 9/00* (2006.01)
*G06T 7/00* (2006.01)
*A61B 3/113* (2006.01)

(52) U.S. Cl.
CPC ............ *G06K 9/0061* (2013.01); *A61B 3/113* (2013.01); *G06K 9/00617* (2013.01); *G06T 7/0016* (2013.01); *G06T 2207/30041* (2013.01)

(58) Field of Classification Search
None
See application file for complete search history.

(56) References Cited

U.S. PATENT DOCUMENTS

| 3,339,206 | A | 9/1967 | Daley | |
|---|---|---|---|---|
| 7,387,387 | B2 | 6/2008 | Dai | |
| 7,520,609 | B2 | 4/2009 | Tuan | |
| 7,565,905 | B2 | 7/2009 | Hickle | |
| 7,856,135 | B1 * | 12/2010 | Bernardes | A61B 3/12 382/131 |
| 8,172,459 | B2 | 5/2012 | Abreu | |
| 8,328,420 | B2 | 12/2012 | Abreu | |

(Continued)

FOREIGN PATENT DOCUMENTS

| EP | 1576523 A2 | 12/2005 |
|---|---|---|
| EP | 1450888 B1 | 2/2011 |

(Continued)

OTHER PUBLICATIONS

Rajesh Jain, published on YouTube Apr. 24, 2012.*

(Continued)

*Primary Examiner* — Mark Roz
(74) *Attorney, Agent, or Firm* — Cantor Colburn LLP; Mercedes Hobson (57) ABSTRACT

A method and system for tracking eye recovery. The method includes: receiving eye data from an eyewear, wherein the eye data includes images acquired by an image capturing device in the eyewear; analyzing the eye data to determine an eye recovery status, wherein the analyzing is carried out by comparing the eye data to an initial set of eye conditions; and providing a notification of the eye recovery status.

15 Claims, 7 Drawing Sheets

(56) References Cited

U.S. PATENT DOCUMENTS

| 8,448,343 | B2 | 5/2013 | Nakako |
| 2007/0066916 | A1 | 3/2007 | Lemos |
| 2011/0026789 | A1* | 2/2011 | Hsu .................... G06K 9/0061 |
| | | | 382/128 |
| 2013/0172691 | A1 | 7/2013 | Tran |
| 2013/0188141 | A1* | 7/2013 | Nakahara ................ A61B 3/14 |
| | | | 351/206 |

FOREIGN PATENT DOCUMENTS

| WO | WO 9849028 A1 | 11/1998 |
| WO | WO 2006009909 A1 | 1/2006 |
| WO | WO 2001089373 A2 | 2/2012 |

OTHER PUBLICATIONS

Charged Coupled Device, Wikipedia, 2004.*
Michelle Green et al., "Reconsidering Yarbus: A Failure to Predict Observers' Task from Eye Movement Patterns," Vision Search, Apr. 2, 12, p. 1-8 v. 62, Elsevier, U.S.
Susana Martinez-Conde et al., "The Role of Fixational Eye Movements in Visual Perception," Nature Reviews, Neuroscience, 2004, p. 229-240 v. 5, Nature Publishing Group.
Claudio Privitera et al., "The Pupil Dilation Response to Visual Detection," Human Vision and Electronic Imaging XIII, 2008, p. 1-11. v. 6806, SPIE IS&T, U.S.
Daniel Richardson et al., "Eye-Tracking: Characteristics and Methods," Encyclopedia of Biomaterials and Biomedical Engr, Feb. 2004, p. 1-32, Wnek G. & Bowlin., G., U.S.
Alfred Yarbus et al., "Eye Movements and Vision," Institute of Problems of Information Transmission Academy of Sci. of the USSR, Moscow, 1967, Plenum Press NY.

* cited by examiner

TRACKING EYE RECOVERY

BACKGROUND OF THE INVENTION

Field of the Invention

The present invention is related to a method and system for tracking eye recovery and more particularly to a data analytics module that uses data collected from an eyewear to track eye recovery.

Description of the Related Art

Tracking the recovery or progress of a person's eyes takes into account multiple different variables. Variables include eye characteristics like physiological conditions and environmental conditions that interfere with the eyes. These conditions influence the recovery of a person's eyes after a surgical procedure.

In ophthalmology medical practice patients are required to wear an eye shield for a period of time to avoid injury while their eyes recover. For example, an eye shield is used after a LASIK eye surgery in which the patient is suggested to restrain from any excess strain or impact to avoid injury to their eyes. Such injury can arise from minor environmental interferences such as dust, light, external pressure, and can result in physiological conditions such as infection, excessive blinking, dry eyes, inflammation, and/or discoloring. Generally, a patient is required to wear an eye shield in post-op treatment. Patients are recommended to avoid high impact activities, avoid straining their eyes, and exposing them to high-intensity light such as: direct sunlight, television, and/or computers. However, the eye shield has many complications and is not customized to each individual's eyes. Every individual's eyes are unique which makes it difficult to determine the progress and recovery of each patient's eyes using a standard method and/or guidelines that is not flexible to a user's eyes.

There is a need to track the post-op recovery for patients for facilitating efficient and smooth recovery that is customized to each patient's eyes. The present invention provides a method, apparatus, and system for tracking eye recovery.

SUMMARY OF THE INVENTION

One aspect of the present invention provides a method for tracking eye recovery. The method includes: receiving eye data from an eyewear, wherein the eye data includes images acquired by an image capturing device in the eyewear; analyzing the eye data to determine an eye recovery status, wherein the analyzing is carried out by comparing the eye data to an initial set of eye conditions; and providing a notification of the eye recovery status.

Another aspect of the present invention provides an eyewear for collecting eye data. The eyewear includes: an image capturing device for capturing images of at least one eye a sensor circuit for detecting environmental conditions affecting the at least one eye and a wireless node for transmitting eye data to a data analytics module, wherein the eye data comprises the images and the environmental conditions.

Another aspect of the present invention provides a data processing system for tracking eye recovery. The system includes a memory; a processor communicatively coupled to the memory; and a data analytics module communicatively coupled to the memory and the processor. The data analytics module is configured to perform the steps of the method including: receiving eye data from an eyewear, wherein the eye data includes images acquired by an image capturing device in the eyewear; analyzing the eye data to determine an eye recovery status, where the analyzing is carried out by comparing the eye data to an initial set of eye conditions; and providing a notification of the eye recovery status.

BRIEF DESCRIPTION OF THE DRAWINGS

The accompanying figures where like reference numerals refer to identical or functionally similar elements throughout the separate views, and which together with the detailed description are incorporated in and from part of the specification, serve to further illustrate various embodiments to explain various principles and advantages all in accordance with the present invention.

DETAILED DESCRIPTION OF THE PREFERRED EMBODIMENTS

As will be appreciated by one skilled in the art, aspects of the present invention can be embodied as a system, method, or computer program product. Accordingly, aspects of the present invention can take the form of an entirely hardware embodiment, an entirely software embodiment (including firmware, resident software, micro-code, etc.) or an embodiment combining software and hardware aspects that can all generally be referred to herein as a "circuit," "module" or "system." Furthermore, aspects of the present invention can take the form of a computer program product embodied in one or more computer readable medium(s) having computer readable program code embodied thereon.

Any combination of one or more computer readable medium(s) can be utilized. The computer readable medium can be a computer readable signal medium or a computer readable storage medium. A computer readable storage medium can be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium can include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium can be any tangible medium that can contain, or store a program for use by or in connection with an instruction execution system, apparatus, or device.

A computer readable signal medium can include a propagated data signal with computer readable program code embodied therein, for example, in baseband or as part of a carrier wave. Such a propagated signal can take any of a variety of forms, including, but not limited to, electromagnetic, optical, or any suitable combination thereof. A computer readable signal medium can be any computer readable medium that is not a computer readable storage medium and that can communicate, propagate, or transport a program for use by or in connection with an instruction execution system, apparatus, or device.

Program code embodied on a computer readable medium can be transmitted using any appropriate medium, including but not limited to wireless, wireline, optical fiber cable, RF, etc., or any suitable combination of the foregoing.

Computer program code for carrying out operations for aspects of the present invention can be written in any combination of one or more programming languages, including an object oriented programming language such as Java, Smalltalk, C++ or the like and conventional procedural programming languages, such as the "C" programming language or similar programming languages. The program code can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The present invention provides a method, apparatus and system for tracking the recovery of an eye and detecting complications in such recovery. The present invention provides a data analytics module which is embedded in a wireless communication device. The data analytics module utilizes technologies such as data mining, machine learning, and pattern recognition, to process the data received from an eyewear. The data analytics module provides alerts on abnormal findings and reminders for adherence improvement using the eye data received from the eyewear.

Figure 1:
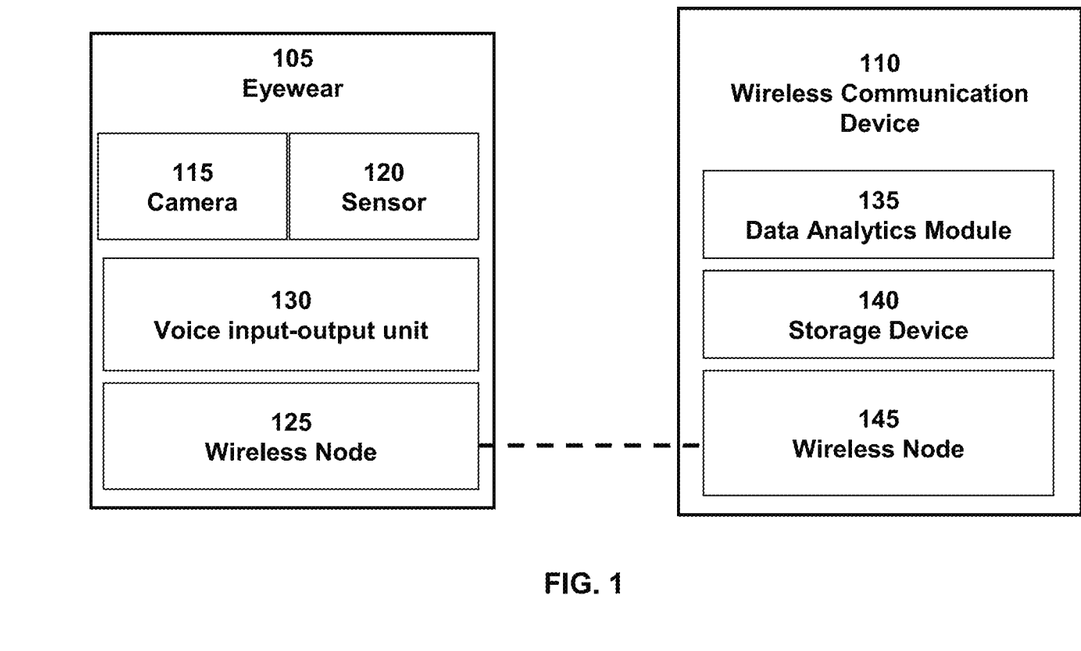
FIG. 1 depicts the system for tracking the recovery of an eye according to an embodiment of the present invention.

FIG. 1 depicts the system for tracking the recovery for at least one eye according to an embodiment of the present invention. The present invention provides an eyewear 105 for collecting eye data on the environmental and physiological conditions of a user's eyes. The eyewear includes at least one image capturing device i.e. camera, situated for the left or the right eye 115 or two cameras for both eyes. In FIG. 1 the eyewear also includes a sensor 120. Each eye of the patient will have a separate camera and sensor. The eyewear stores the eye data collected from the camera 115 and sensor 120 and transmits it to the wireless communication device 110. The wireless communication device 110 receives the eye data from the eyewear 105. The wireless communication device includes or is connected to a data analytics module 135. The data analytics module includes a model to analyze the data to determine an eye recovery status and compares the data received from the eyewear to an initial set of conditions. Thereafter, the data analytics module provides a notification of the eye recovery status. The eye recovery status is stored in the storage device 140. The eyewear and the wireless communication device communicate via a wireless connection. The wireless connection is established between the wireless node 125 in the eye wear and the wireless node 145 in the wireless communication device.

According to the present invention, the wireless communication device can vary. The wireless communication device can be a personal computer, a portable PDA or web-enabled wireless phone i.e. smart phone, or any device suitable for wireless communication known in the relevant art.

According to the present invention, the camera in the eyewear is able to capture images of the eyes at different frequencies. The memory in the eyewear can then store the images to be analyzed by the data analytics module. The camera can be programmed to capture images at a certain time, frequency, and/or settings. The images of each eye are used to determine the physiological conditions of the eye. For example pupil dilation, coloring, size of eye, eye circulation, eye ball movement, strain on the eye, eye blinking, and any other conditions known in the relevant art.

According to another embodiment of the present invention, the image capturing device can be a real-time recording device to create a video for at least one eye for a certain period of time. The recording device can capture a video and send it to the data analytics module to be analyzed. The recording device will assist in determining physiological conditions of the eye. For example: pupil dilation, coloring, size of eye, eye circulation, eye ball movement, strain on the eye, eye blinking, and any other conditions known in the relevant art.

According to another embodiment of the present invention, the eyewear can include a pressure sensor and a motion sensor to detect environmental conditions interfering with the eye. For example, a motion sensor can detect head turns, movements surrounding the eye, or other conditions known in the relevant art. If the sensor is a pressure sensor it can detect a user's touch, a user's rub, external debris, skin moisture, swelling, and any other conditions known in the relevant art. The sensor can include a pressure and a motion sensor as known in the relevant art.

According to another embodiment the present invention, the initial set of conditions can be baseline conditions. Baseline conditions can be eye data collected before an ophthalmologic procedure is performed on a user. According to the present invention, the user wears the eyewear for a period of time before the procedure. During the period of time the eyewear collects eye data using the camera and/or the sensor. The eye data is then transmitted to the wireless communication device that stores the information in a memory. The wireless communication device includes or is connected to a data analytics module that analyzes the eye data. The data analytics module compares the eye data received after the ophthalmologic procedure to the baseline conditions acquired before the ophthalmologic procedure. The data analytics module determines the compliance to the baseline conditions and uses the results to provide a notification of the eye recovery status.

According to an embodiment of the present invention, the data analytics module can produce an entire eye recovery report. An eye recovery report can have multiple aspects of the eye recovery status. For example, the eye recovery report can have a detailed description of the progress, the new recommendations for medication intake, a comparative analysis between the left and right eye, a comparative analysis with the EMR data, a comparative analysis with the baseline conditions, and/or any other progress details known in the relevant art.

According to another embodiment of the present invention, the initial set conditions can include the user's electronic medical record (EMR). The EMR data can include diagnosis, lab results, medication, and/or hospitalization records. The EMR can be stored in the memory of the wireless communication device or it can be stored on a cloud computing service system that is connected to the data analytics module via a specified wireless connection to the wireless communication device.

According to other embodiments of the present invention, the initial set of conditions can include eye data inserted by the user which includes, but not limited to, a plurality of predetermined threshold values for certain physiological or environmental characteristics. For example, blink frequency of the eye. According to an embodiment of the present invention, the data analytics module can be programmed so that when the eye recovery status indicates that predetermined threshold values are surpassed then an alert system will notify a user who is wirelessly connected to the data analytics module. In another embodiment of the present invention, multiple users can be connected to the data analytics module so that multiple users can be notified when a predetermined threshold has been surpassed. The multiple users can be connected by wireless connections and/or cloud computing services or any other suitable methods known in the relevant art.

According to the present invention, the data analytics module is a computer-implemented method for analyzing the eye data and generating a recovery report. The method is for detecting patterns and correlations in signs and symptoms for at least one eye. The data analytics module applies a model to analyze the eye data. The model performs a comparative analysis between prior data and current eye data. For example, between images captured of the eye before the ophthalmologic procedure and after the ophthalmologic procedure. The model performs an analysis of the images for a region of interest, for instance on the eye ball and/or eyelid. According to an embodiment of the present invention, the data analytics module analysis can be divided into sclera and pupil of the eye. The data analytics module will analyze the eye data by performing a texture and color analysis of the distinct portions of the eye. The data analytics module can detect recovery status of the eye by performing the sclera and pupil texture and color analysis.

According to another embodiment of the present invention, the model includes the ability to quantify eye characteristics. Eye characteristics include blinking frequency, which is dependent on what mode a user is experiencing. More specifically, if a person is in relaxed or active mode. Additional eye characteristics include: head turns, hand touch/pressure, and/or motion/speed or any other eye characteristics known in the relevant art. In another embodiment of the present invention, the model can collect a user's self-assessment feedback log and analyze the log relative to the eye data provided by the eyewear to generate the recovery report. Self-assessment factors can include feelings of grittiness, eye strain, itchiness, and/or any other factors known in the relevant art.

According to another embodiment of the present invention, the data analytics module can facilitate the eyewear to collect accurate and real-time adjustable data. Specifically, if the data analytics model needs additional eye data to generate a sufficient recovery report it can communicate and request the eyewear to capture more images or to quantify more eye characteristics. For example, if the data analytics module determines that the eye data contains an outlier, or a photo in question, the data analytics module can request the eyewear to capture another image of the eye. The communication can be accomplished via a wireless connection between the eyewear and the wireless communication device or any other suitable methods known in the relevant art.

Referring to FIG. 1, the eyewear can include a voice input-output unit 130. The voice input-output unit allows the user to speak to the voice input and receive a response through the voice output. The eyewear will send the request to a wireless communication device via the wireless node and receive the answer from the wireless communication device. The voice output will respond with an answer via a microphone. For example, if a user asks about the weather, the eyewear will send the request to the wireless communication device, in this case a smart phone, the smart phone will search for the answer on the internet, and send the answer back to the eyewear device which will relay the answer to the user.

According to another embodiment of the present invention, the voice input-output unit is an automatic switching circuit used in the eyewear and/or the wireless communication device. The voice input-output unit can be programmed or customized to include many features such as: a) data collection: enabling a user to orally give self-assessment feedback, such as feelings of itchiness, burning, etc., into the system; b) communication and interaction: patients can have simple conversations with the device, such as "is it raining heavily outside?"; c) timer/reminder: device can be preprogrammed to keep track of when to remind patients to take eye drops or oral meds during what time interval; and/or d) alerting: device can generate sound alarm for "inappropriate" behaviors such as watching too much TV, or computers. The voice input-output unit enables the user to utilize the data analytics module and the wireless communication device without having to strain his/her eyes to use a keyboard.

According to the present invention, the eyewear includes a memory. The memory can store the information collected from the camera and/or sensors until it is to be transferred to the wireless communication device.

According to an embodiment of the present invention, the wireless communication device is a smart phone and the data analytics module is a phone application installed on the smart phone.

According to another embodiment of the present invention, the data analytics module includes an alert system for setting reminders for medication or reminders for a medication that was missed. The alert system can be a programmable so that the user can input specific times to set voice and/or sound notifications. For example, times to apply eye medicine based on a prescribed frequency. The alarm can be transmitted using a speaker on the eyewear and/or on the wireless communication device.

Another embodiment of the present invention, allows a user to specify time intervals in the data analytics module to provide an eye recovery status at the specified time intervals.

Figure 2:
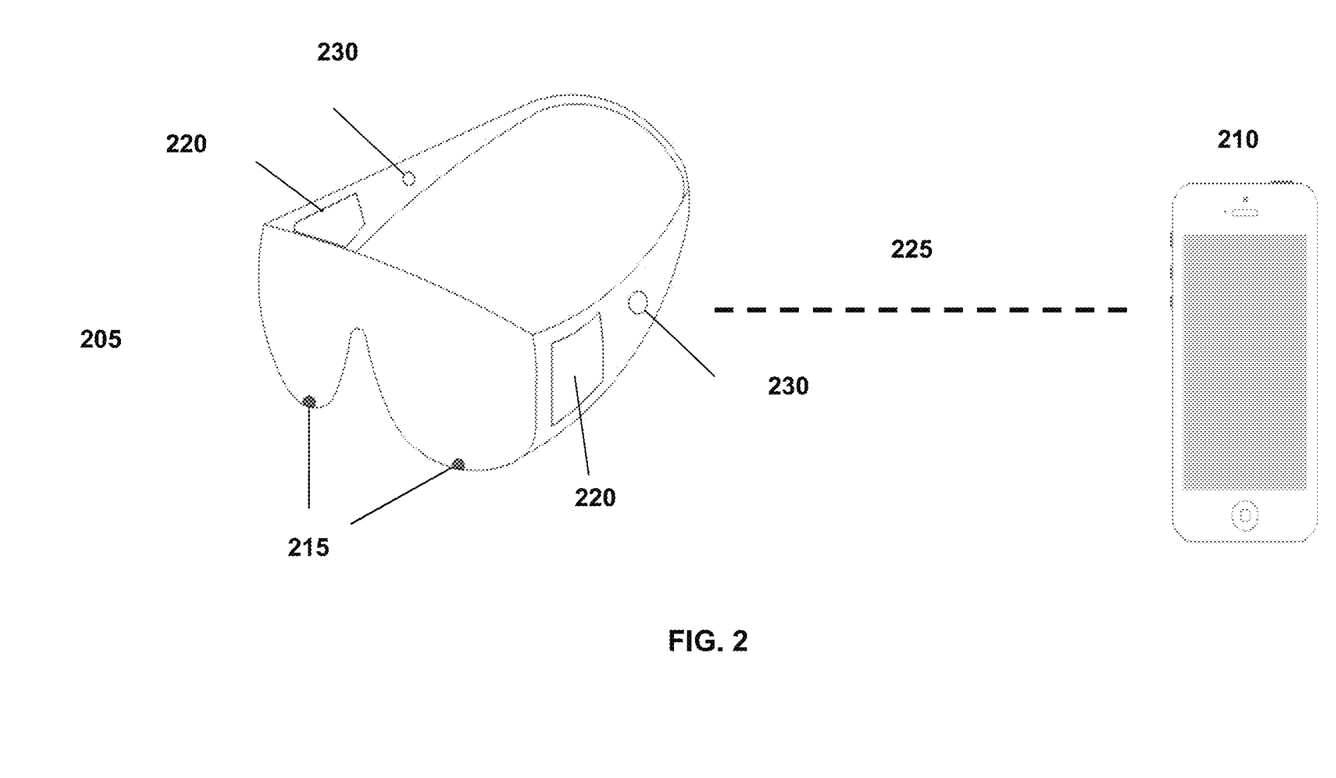
FIG. 2 depicts an eyewear connected to a smart phone via a wireless connection according to a further embodiment of the present invention.

FIG. 2 depicts an eyewear connected to a smart phone via a wireless connection according to an embodiment of the present invention. The eyewear 205 is an eye shied with at least one wearable camera 215, sensor 220, and a voice input-output unit 230. The wireless communication device 210 is depicted as a smart phone. The smart phone includes the data analytics module smart phone application installed in it (not shown). The smart phone and the eyewear communicate via a wireless connection 225. In an embodiment of the present invention the wireless connection is Blue Tooth 4.0 connection.

According to another embodiment of the present invention, the data analytics module can be stored on a second wireless communication device so that the analysis can run on the second wireless communication device. The second wireless communication device can be a personal computer or a cloud computing service or any other suitable wireless communication device to run the data analytics module.

Referring to FIG. 2, the eyewear 205 is a long time wearable device that should fit on a user's head. The eyewear includes a battery operated power source or any other suitable power source known in the relevant art.

Figure 3:
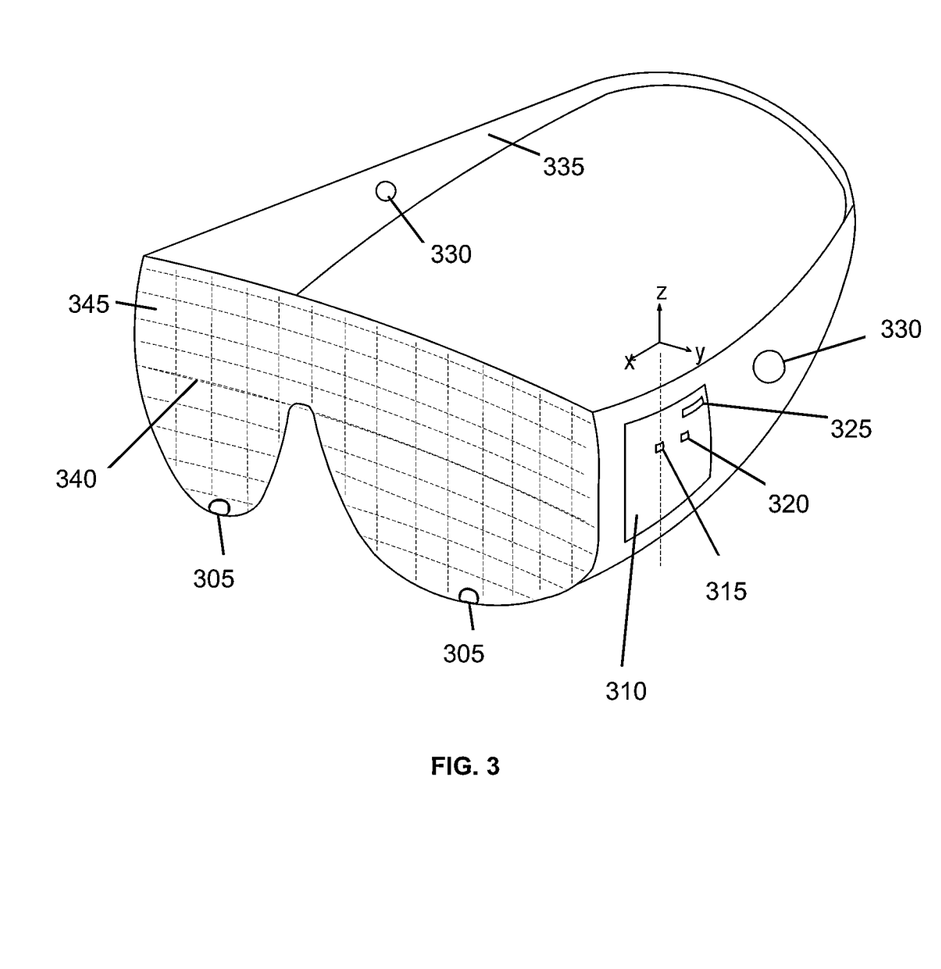
FIG. 3 depicts an eyewear according to a further embodiment of the present invention.

FIG. 3 depicts an eyewear according to an embodiment of the present invention. The micro-cameras 305 are located at the bottom center of each lens so that it can capture images of both eyeballs. The micro-cameras can be any suitable camera known in the relevant art that can capture images of the eyeball and the surrounding area. The cameras are located on each lens so that there is a left-eye micro camera and a right eye micro-camera. The sensor circuit 310 is located at the sides of each eye to collect eye data which is later transmitted to the data analytics module. The sensor circuit can detect environmental conditions. Preferably, the sensor circuit is a flexible circuit board. As shown in FIG. 3 there can be only one sensor. The sensor circuit can include, but is not limited to, an axis accelerometer 315, an inter-digital capacitor 320 sensor and a wireless node 325. An accelerometer can detect any acceleration which includes movement. The accelerometer 315 used for the sensor can be a 3-axis accelerometer for movement detection, movement detection includes head movement or movement surrounding the eyes. The sensor circuit can include an inter-digital capacitor sensor for moisture detection 320. The sensor circuit can include a wireless node. Preferably, a wireless node that supports Bluetooth 4.0 for data transmission.

Referring to FIG. 3, the eyewear can also include a voice input-output unit 330. As discussed above, the voice input-output unit can be a speaker/microphone that can make sounds and/or voice alerts according to the user's prescribed times to take medication and such. Preferably, the voice input-output unit is located near each ear of the user, as shown in FIG. 3.

Referring to FIG. 3, the eyewear is a wearable soft permeable material 335. According to an embodiment of the present invention the eyewear should be worn through the night so that it can collect eye data when the user is sleeping. Preferably, the material of the eyewear is soft and comfortable.

Referring to FIG. 3, the eyewear can include a pressure sensor 340. The pressure sensor can be a transparent capacitor matrix pressure sensor at the lens of the eyewear. The pressure sensor can detect pressure impact on the user's eye. Conditions can include a user rubbing his/her eyes, an external impact on the user's eyes, and/or any other external pressure conditions known in the relevant art. Accordingly, the transparent capacitor matrix pressure sensor can detect deformation and pressure.

Referring to FIG. 3, the eyewear can include an ultraviolet (UV) coating for light protection 345. This UV coating can be adjusted according to the user's procedure and the amount of sunlight that recommended for the user. The UV coating can change according to the lighting conditions so that the eyewear will automatically change color. The UV coating can be adjusted to the user's sensitivity and/or according to the specific purpose of the eyewear. Suitable methods of UV coating on the eyewear can be determined by the person with ordinary skill in the art.

According to the present invention, the eyewear protects the eyes of a user as an eye shield. The strap adjustment of the eyewear and quick release mechanisms are simple to use and enables the eyewear to be adjusted while in place on the head of the user to fit the user in a manner to create a water-tight/air-tight seal (fluid-tight seal) around the user's eyes in a manner to conform to the contours of the user's face and avoid irritation of the skin from prolonged use. The lenses that are used in the eyewear are capable of being manufactured to prescription specifications and can include sunlight protection as known in the relevant art.

In another embodiment of the present invention, the eyewear is in the form of eye glasses. Accordingly, the eyewear can be secured to a user's head with two arms curved at each end to form ear hooks as is normal with eye glasses.

According to another embodiment of the present invention, the eyewear includes the data analytics module within the eyewear. The data analytics module can be divided into a back-end processing system and a front-end processing system. The back-end processing system can do the analyzing and comparative analysis and the front-end processing system which can process the alerts and reminders from the image capturing device and the sensors. Both the back-end processing and the front-end processing system can run on the eyewear itself, wireless communication device, and cloud computing service, and any other suitable module known in the relevant art. In another embodiment of the present invention, the front-end processing system and the back-end processing system can be divided so that the front-end processing system can run on the eyewear and the back-end processing system can run on the wireless communication device, cloud computing system or any other suitable module known in the relevant art.

According to an embodiment of the present invention, the eyewear includes a vibration speaker. The vibration speaker will transmit sound to its user via vibrations through human bones, rather than using traditional speakers. The vibration speaker uses sound transmission system that transmits sounds to the user's bones without the use of typical ear-buds or speakers as known in the relevant art.

Figure 4:
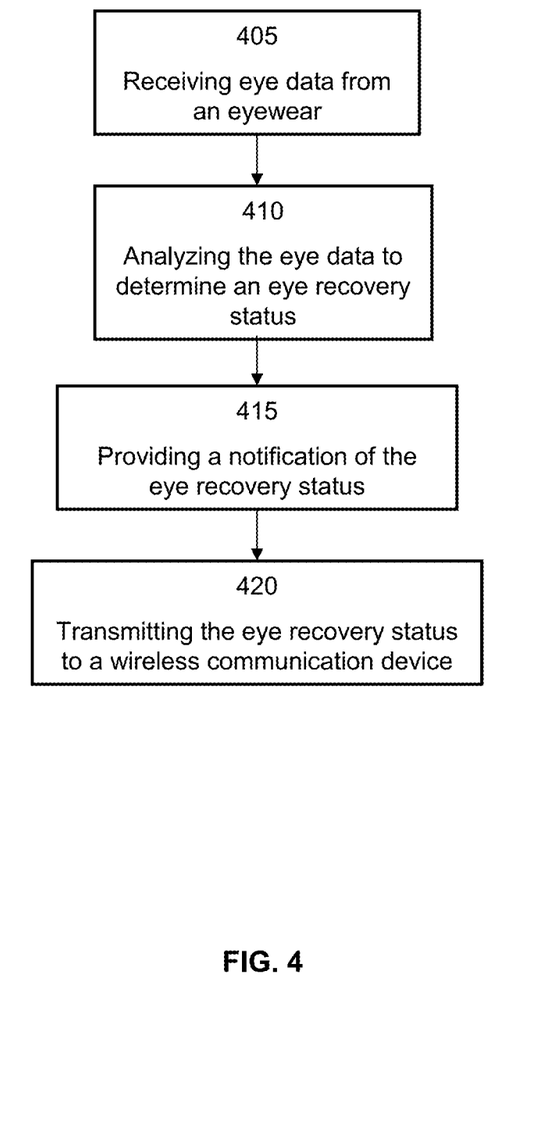
FIG. 4 depicts the process of tracking the recovery of an eye according to a further embodiment of the present invention.

FIG. 4 depicts the process of tracking the recovery of an eye according to an embodiment of the present invention. In step 405 the data analytics module is receiving eye data from an eyewear. In step 410 the data analytics module is analyzing the eye data to determine an eye recovery status. In step 420 the data analytics module is providing a notification of the eye recovery status. Next, in step 425 the data analytics module is transmitting the eye recovery status to a wireless communication device.

According another embodiment of the present invention, the wireless communication device that includes the data analytics module can be connected to other wireless communication devices utilizing a cloud computing service. More specifically, the recovery report can be transmitted to multiple users utilizing a cloud computing service and/or wireless connections.

According to an embodiment of the present invention, EMR (with longitudinal data) will be stored in cloud which can be stored in one care provider's office or multiple providers' office, since a user can have more than one provider. Thereafter, a user can download a copy or partial copy of EMR from the cloud/server to his/her own wireless communication device. As eye data is collected from the eyewear for at least one eye it can be stored in the memory of the wireless communication device and uploaded periodically to the cloud. The uploading frequency can be programmed and set according to the recovery status and/or user preferences. The data analytics module will perform the steps to generate a recovery report on the cloud computing service. According to an embodiment of the present invention, the simple computing can be accomplished on the mobile device, such as visualization, alerts/reminders, and/or the like.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 4, a schematic of an example of a cloud computing node is shown. Cloud computing node is only one example of a suitable cloud computing node and is not intended to suggest any limitation as to the scope of use or functionality of embodiments of the present invention described herein. Regardless, cloud computing node is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

Figure 5:
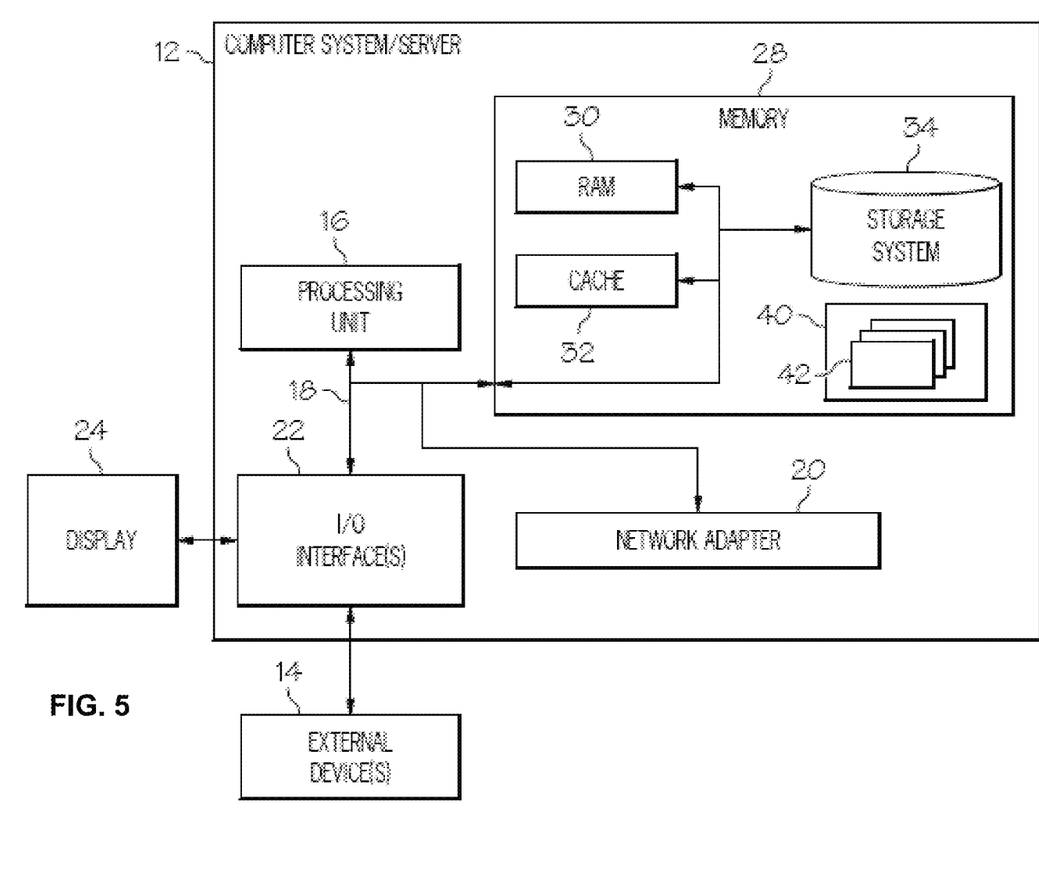
FIG. 5 depicts a cloud computing node according to a further embodiment of the present invention.

As shown in FIG. 5, computer system/server 12 in cloud computing node 10 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components can be used in conjunction with computer system/server 12. Examples, include, but are not limited to: microcode, device drivers, redundant processing units, external disk drive arrays, RAID systems, tape drives, and data archival storage systems, etc.

Referring now to FIG. 5, an example illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
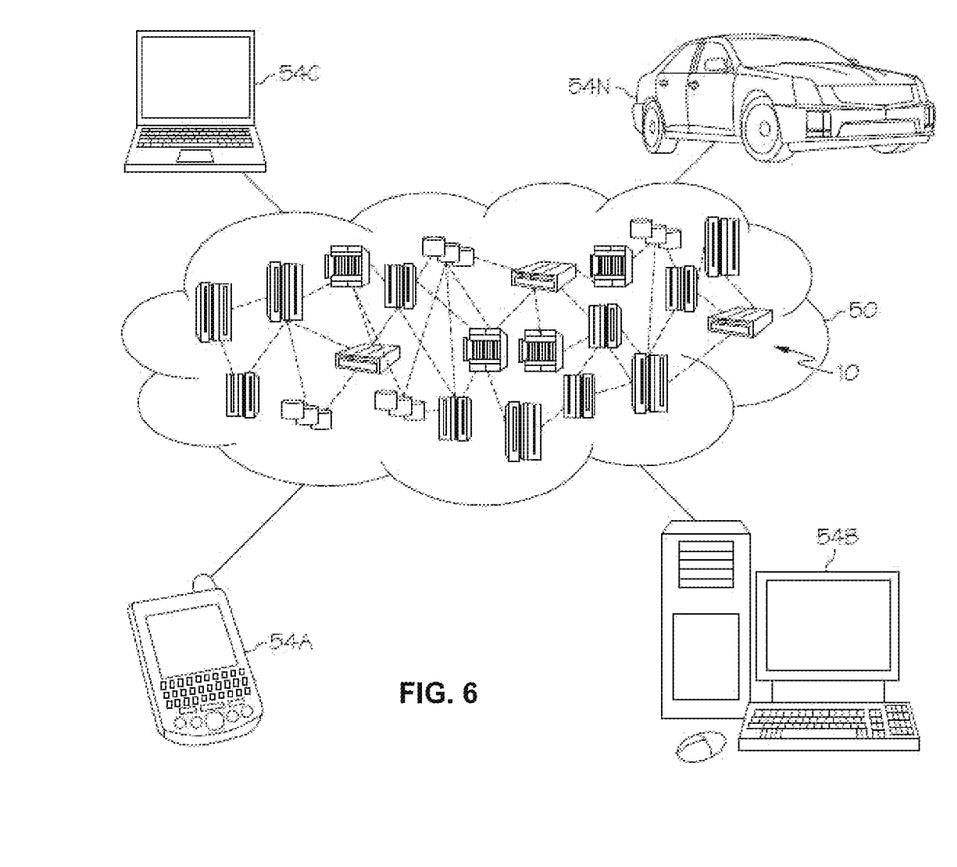
FIG. 6 depicts a cloud computing environment according to a further embodiment of the present invention.
Figure 7:
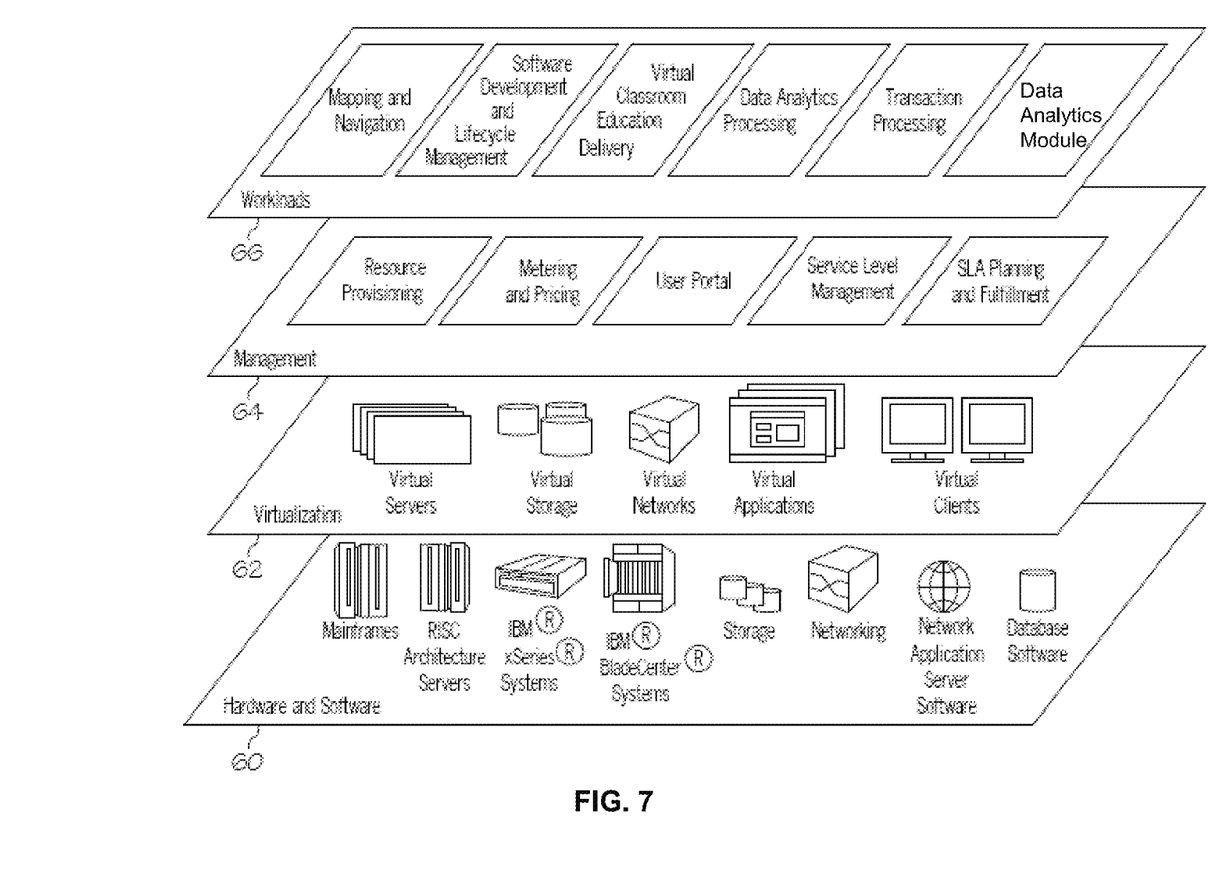
FIG. 7 depicts abstraction model layers according to a further embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems;

IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities can be provided: virtual servers; virtual storage; virtual networks, including virtual private networks; virtual applications and operating systems; and virtual clients.

In one example, management layer 64 can provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources can comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment can be utilized. Examples of workloads and functions which can be provided from this layer include: mapping and navigation; software development and lifecycle management; virtual classroom education delivery; data analytics processing; transaction processing; and Data Analytics Module (described in detail above).

The flowchart and block diagrams in the Figures illustrate the architecture, functionality, and operation of possible implementations of systems, methods and computer program products according to various embodiments of the present invention. In this regard, each block in the flowchart or block diagrams can represent a module, segment, or portion of code, which comprises one or more executable instructions for implementing the specified logical function (s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for tracking eye recovery of a user, the method comprising:
   detecting non-light environmental conditions affecting at least one eye of the user using a sensor circuit integrated into an eyewear, wherein the non-light environmental conditions include head movement of the user;
   capturing an image of the at least one eye of the user using an image capturing device integrated into the eyewear;
   receiving, from the eyewear, eye data at a wireless communication device that comprises a data analytics module, wherein the eye data comprises the image captured by the image capturing device in the eyewear and the non-light environmental conditions detected using the sensor circuit;
   analyzing, using the data analytics module, the eye data to determine an eye recovery status, wherein the analyzing is carried out by comparing the eye data to an initial set of eye conditions;
   generating, using the data analytics module, an eye recovery report using the eye data and the eye recovery status;
   providing a notification of the eye recovery status; and
   transmitting the eye recovery report to the user of the eyewear.

2. The method of claim 1, wherein the initial set of conditions comprises baseline conditions acquired before tracking eye recovery.

3. The method of claim 1, wherein analyzing the eye data to determine eye recovery status comprises comparing an eye data from a left eye to an eye data of a right eye.

4. The method of claim 1, wherein analyzing the eye data to determine eye recovery status comprises comparing the eye data to a plurality of predetermined threshold values.

5. The method of claim 4, further comprising sending an alert message in response to the eye data surpassing the plurality of predetermined threshold values.

6. The method of claim 1, wherein analyzing the eye data to determine eye recovery status comprises comparing the eye data to an electronic medical record (EMR) data.

7. The method of claim 6, wherein the EMR data is located on a wireless communication device and is accessible through a cloud computing service.

8. The method of claim 1, wherein analyzing the eye data to determine eye recovery status comprises analyzing user's self-assessment feedback log inputted into the data analytics module.

9. The method of claim 1, further comprising facilitating the eyewear device to collect a real-time adjustable eye data.

10. A data processing system for tracking eye recovery of a user, the system comprising:
    a memory;
    a processor communicatively coupled to the memory; and
    a data analytics module communicatively coupled to the memory and the processor, wherein the data analytics module is configured to perform the steps of a method comprising:
    detecting non-light environmental conditions affecting at least one eye of the user using a sensor circuit integrated into an eyewear, wherein the non-light environmental conditions Include head movement of the user;
    capturing an image of the at least one eye of the user using an image capturing device integrated into the eyewear;
    receiving, from the eyewear, eye data at a wireless communication device that comprises a data analytics module, wherein the eye data comprises the image captured by the image capturing device in the eyewear and the non-light environmental conditions detected using the sensor circuit;

analyzing, using the data analytics module, the eye data to determine an eye recovery status, wherein the analyzing is carried out by comparing the eye data to an initial set of eye conditions;

generating, using the data analytics module, an eye recovery report using the eye data;

providing a notification of the eye recovery status; and transmitting the eye recovery report to the user of the eyewear.

11. The data processing system of claim 10, wherein the data analytics module is a wireless communication device.

12. The data processing system of claim 11, wherein the wireless communication device is a smart phone.

13. The method of claim 1, wherein the eye recovery report comprises at least one from a group consisting of a detailed description of recovery progress, a new recommendations for medication intake, a comparative analysis between a left and right eye, a comparative analysis with (EMR) data, a comparative analysis with baseline conditions, and progress details.

14. The method of claim 1, wherein the sensor circuit includes one or more from a group consisting of a pressure sensor, a transparent capacitor matrix pressure sensor, a motion sensor, a flexible circuit board, an axis accelerometer, an inter-digital capacitor, and a wireless node.

15. The method of claim 1, wherein non-light environmental conditions include dust, external pressure, head turns, movements surrounding the eye, a user's touch, a user's rub, external debris, skin moisture, swelling, blink frequency of the eye.

* * * * *